United States Patent [19]

Laboureau

[11] Patent Number: 4,787,377
[45] Date of Patent: Nov. 29, 1988

[54] SURGICAL INSTRUMENT FOR POSITIONING AND INSERTION OF POSTERIOR CRUCIATE LIGAMENT OF THE KNEE IN PLASTY (OR PROSTHETIC REPLACEMENT)

[76] Inventor: Jacques-Philippe Laboureau, 24, rue de la Fontaine Billenois, 21000 Dijon, France

[21] Appl. No.: 47,858

[22] Filed: May 6, 1987

[51] Int. Cl.$^4$ .............................................. A61F 5/04
[52] U.S. Cl. .......................... 128/92 VD; 128/92 V; 128/303 R
[58] Field of Search .............. 128/321, 323 R, 92 VZ, 128/92 VD, 92 V, 92 VK

[56] References Cited

U.S. PATENT DOCUMENTS

| | | | |
|---|---|---|---|
| 3,867,932 | 2/1975 | Huene | 128/92 VD |
| 4,257,411 | 3/1981 | Cho | 128/92 VD |
| 4,312,337 | 1/1982 | Donohue | 128/92 VD |
| 4,364,381 | 12/1982 | Sher et al. | 128/92 VD |
| 4,444,180 | 4/1984 | Schneider et al. | 128/92 VD |
| 4,535,768 | 8/1985 | Hourahane et al. | 128/92 VD |

Primary Examiner—Stephen C. Pellegrino
Assistant Examiner—Colleen M. Reilly
Attorney, Agent, or Firm—Gregory O. Garmong

[57] ABSTRACT

This invention concerns a surgical instrument for positioning and insertion for plasty (prosthetic replacement) of the posterior cruciate ligament of the knee.

This instrument is characterized by the fact that it consists of, on the one hand, a chisel composed of a handle (2) and a blade (1) in the shape of an italic 'S', the internal terminal part of which (4) is concave, so that the aforesaid blade (1) may be introduced across the femoral notch up to the posterior face of the tibia, and on the other hand, a guide support (9) fixed firmly to the chisel (1, 2) by clamp (8), which comprises at its extremity, arranged in relation to and at a distance from the concave part (4) of the blade (1), two double branch guides (10) in the direction of the aforementioned concave part (4).

7 Claims, 3 Drawing Sheets

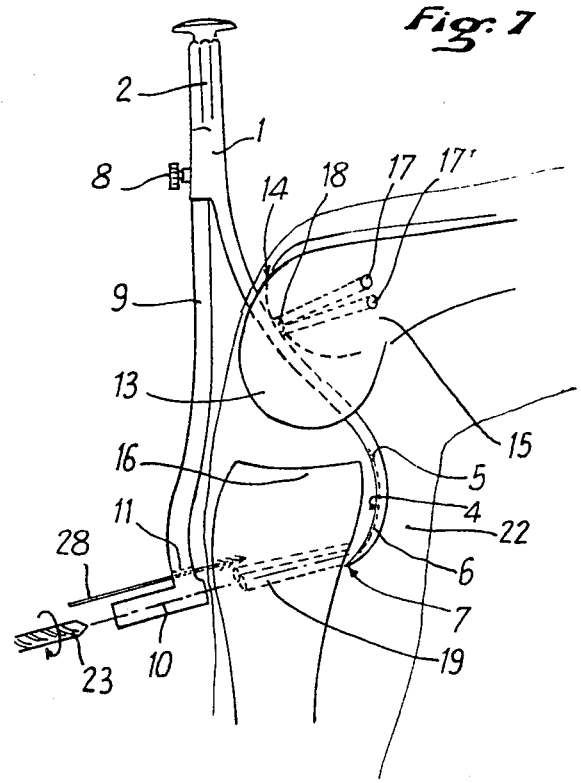
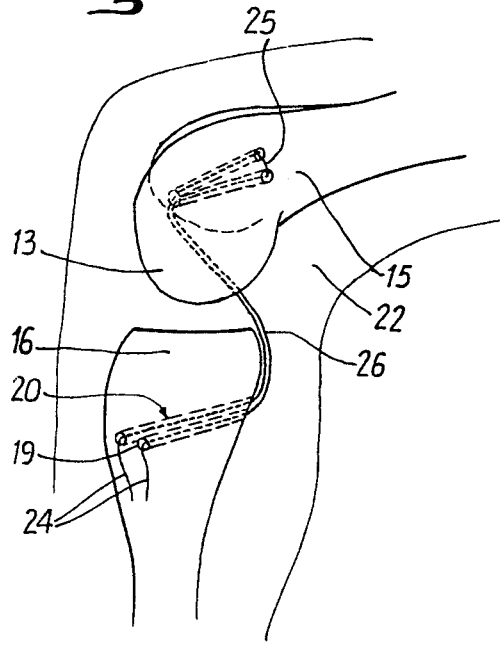
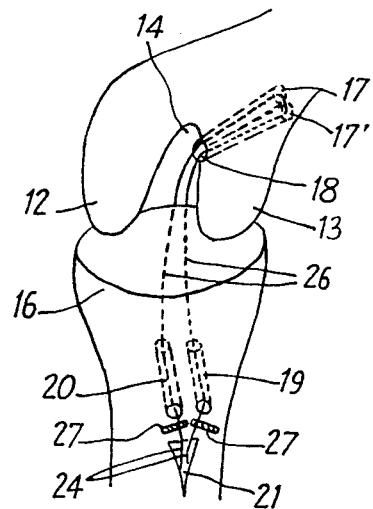

SURGICAL INSTRUMENT FOR POSITIONING AND INSERTION OF POSTERIOR CRUCIATE LIGAMENT OF THE KNEE IN PLASTY (OR PROSTHETIC REPLACEMENT)

BACKGROUND OF THE INVENTION

This invention concerns a surgical instrument for positioning and insertion for plasty (or prosthetic replacement) of the posterior cruciate ligament termed herein the "pcl") of the knee.

When a consecutive ligamentary rupture occurs, for example, by accident, it is well known that it may be necessary to proceed to replace one or some of the damaged ligaments. Some of the ligaments cannot repair themselves: this is notably the case with the posterior cruciate ligament of the knee.

The difficulty in replacing this ligament is no longer linked to the ligament itself, since nowadays many suitable methods for replacement of artificial ligaments are well known. On the other hand, the surgery associated with these type of operations demonstrates many inconveniences, linked particularly to anatomical problems.

In fact in order to replace a PCL, it is of course necessary to operate on the femoral condyl, thus from the front of the patient's knee, but also on the posterior of the tibia, that is the back of the patient's knee. All this therefore presents difficult manipulations of the patient within the operating situation, on the surgical table, in an environment in which both available space and time to act are limited.

SUMMARY OF THE INVENTION

This invention purports to remedy these inconveniences by presenting a surgical positioning and insertion instrument for plasty (or surgical replacement) of the posterior cruciate ligament of the knee. The instrument permits this surgery to be carried out from a medial parapatellar approach, whilst enabling an anatomical point of penetration of the aforesaid PCL at the posterior face of the tibia, thus avoiding any wound to the posterior elements, which are notably vascular. The invention consists of:

on the one hand, a chisel composed of a handle and a blade in the form of an italic 'S', the end part of which is concave, so that the blade can be introduced across the femoral incision up to the posterior face of the tibia.

On the other hand, a positioning device firmly anchored to the chisel by clamping means. The positioning device includes at its extremity, arranged in relation to and at a distance from the concave part of the blade, a double branch guide joined in the direction of the aforementioned concave section of the blade. The guide is joined at oblique angle such as the angle formed by the prolongation of the axis of the guides and the tangent at the internal angle of the concave part of the blade, at their meeting point is greater than 90 degrees. The length of the guides is sufficient to ensure the longitudinal guidance of the drills utilised for transversal perforation of the two channels within the tibial section, thus enabling the simultaneous positioning of two internal-posterior and external-posterior parts of the posterior cruciate ligament.

According to the invention, the instrument includes, at the end of the chisel, a cutting edge in the form of a bevelled edge for removing, by scraping along the posterior approach of the tibia, the elements attached to the aforesaid tibia, at a height determined by an angle formed at the interior of the concave blade of the chisel, this angle being viewed by the operator within the inter-articular cavity; when the angle coincides with the top of the tibia, the disengagement of the posterior face of the tibia is thus sufficient to carry out the perforation of both channels destined eventually to receive, in order to anchor them, the parts of the ligamentary prosthesis, previously shaped into a 'U' turn. The chisel, always in the inter-articular position, the cutting edge resting on the posterior approach of the tibia, thus receives the "branch holder" at the front of the patient's tibia; the two joined branches are thus situated perpendicularly at the medial parapatellar approach to the tibia, following the colinear axes, the elongations of which each culminate at the interior of the concave section of the chisel and form an oblique angle in the vertical plane such that the angle formed between them and the tangent of the chisel blade at their meeting point, is obtuse.

Thus positioned, the instrument makes it possible to effect, by the means of a piercing instrument with a drill, the perforation of the two trans-tibial tunnels with the following correlating advantages:

the drill is perfectly guided into the bone mass.

when the aforementioned drill emerges in the posterior section of the tibia, it cannot cause any wound to the vascular clump which is protected by the concave face of the chisel blade.

the axis of each of the tunnels obtained in this manner forms an oblique angle largely facilitating the positioning procedure of the prosthesis.

After withdrawal of the perforation equipment, the complete instrument remains in position, possibly held by a steel pin inserted in a hole designed for this purpose, just above the double branch guides and embedded in the bone. Two flexible pins are introduced, furnished at their extremities with an eyelet up to the point where they meet the concave section of the chisel blade. The pins are inserted at an obtuse angle imposed on the aforementioned pins as the only direction of being inserted towards the interior of the blade following two parallel furrows extending at least from the point of meeting the pin-blade up to about 10 mm above the positioning incision already mentioned.

When the flexible pins appear in the inter-condylar notch, they can be grasped in order to fasten there the two extremities of the 'U' shaped ligament, previously threaded into two tunnels bored from a single point in the inter-condylar notch. This point forms the anatomical point of femoral insertion of the PCL and culminates in the extra-synovial area, above the condylar cheek, following two orifices distanced by one centimeter apart enabling the instantaneous grasping of the base of the 'U' turn of the ligament.

All that remains is to withdraw the two flexible pins by reversing them through their passage, which gives the advantage of automatically threading in the two ligamentary parts from front to back into the two trans-tibial tunnels.

Thus recovered at the medial parapatellar approach of the tibia, the parts are sufficiently taut so that the posterior tilt is equal to zero; the two extremities of the aforesaid parts are thus anchored on the tibia by two specialised staples.

BRIEF DESCRIPTION OF THE DRAWINGS

Hereunder is described, as a non-limiting example, a method of carrying out this invention, with reference to the attached diagram in which:

FIG. 7 is a longitudinal cross-section view of the knee showing the complete surgical instrument according to the invention in effective working position.

FIG. 8 is a longitudinal cross-section view of the knee similar to that in FIG. 7, showing the positioning of the parts of the posterior cruciate ligament (PCL).

FIG. 9 is a perspective view of the articulation of the knee with its artificial PCL in final position.

DETAILED DESCRIPTION OF THE PREFERRED EMBODIMENT

Figure 1:
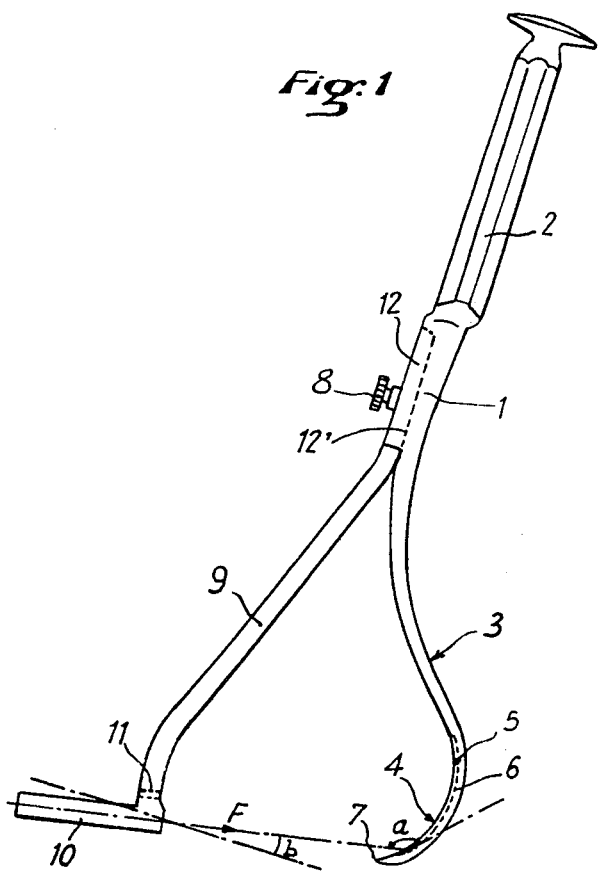
FIG. 1 is an elevated view of the complete surgical instrument according to the invention, comprising the chisel and guide.

The surgical instrument according to the invention, as shown in FIG. 1, is composed of two main functional parts:

A chisel 1 consisting of a handle 2 to facillitate the manipulation of a curved blade in the shape of an italic 'S', the handle 2 being fixed at the end of the upper part 3 of the 'S', the lower part 4 being concave in a similar manner to an extended spoon.

a guide support 9, bearing two joined branches 10 and 10', fixed, at the desired location, to the chisel 1 by insertion of its end 12 into a groove 12' designed for this purpose in the handle 2 of the chisel 1, the whole being anchored by a screw with an adjustable head 8, in such a way that the relative position of the device 9 and of the chisel 1 always permits great accuracy.

Figure 2:
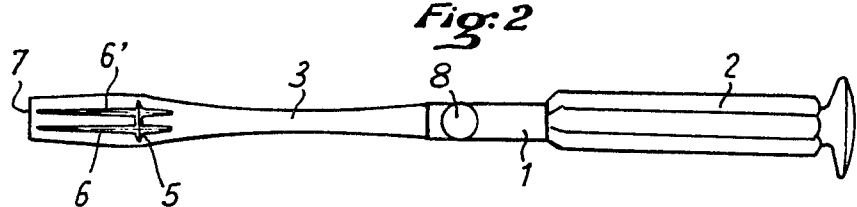
FIGS. 2 and 3 are respectively views of the chisel alone showing the internal and concave section of the blade and a side view of the same chisel.
Figure 3:
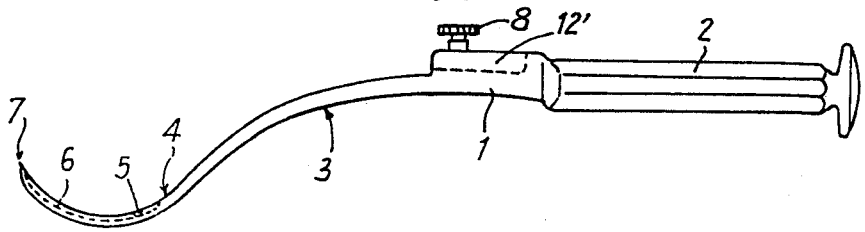
Figure 6:
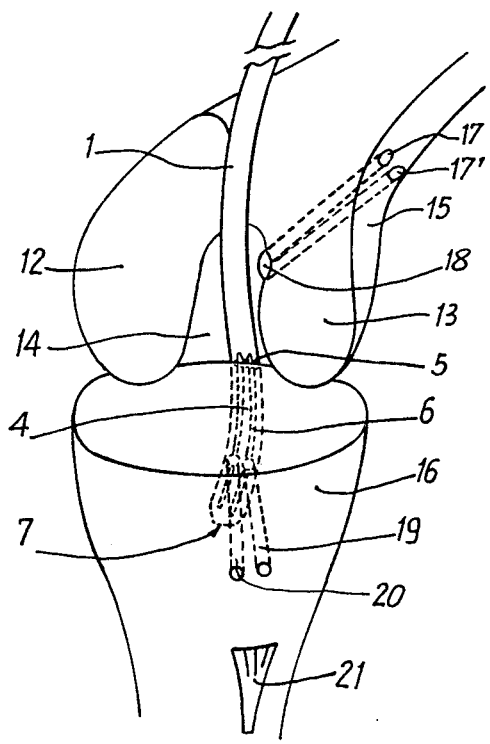
FIG. 6 is a perspective view of the femur/tibia articulation showing, situated in the inter-condyliar notch, part of the chisel blade in its working position.

In accordance with FIGS. 2 and 3, the chisel 1 shows a blade the curves 3 and 4 of which have been strictly worked out, on the one hand, in order to penetrate across the inter-condylar notch 14 shown in FIGS. 6 and thereafter and, on the other hand, in order to descend the length of the posterior face of the tibia 16 carefully following the anatomical form of the tibia.

The chisel 1 is furthermore furnished with a cutting edge 7 enabling dissection by scraping off all the elements attached to the posterior face of the tibia 16 at a height of approximately 40 mm from the superior edge of the tibia, the descent of the blade being controlled by an angle 5 drawn transversally at the interior of the internal concave part 4 of the aforesaid blade; this angle 5 is easily viewed by the operator across the femoral notch 14.

Furthermore, extending longitudinally at the interior of the concave part 4 of the blade, approximately from the cutting edge 7 where they finish, up to a distance of about 10 mm above the angle 5, two parallel grooves are drawn wide enough to ensure certain guidance of a flexible pin, as will be described further on.

Thus constituted, chisel 1 is lowered in accordance with FIG. 6 along the posterior approach of the tibia, the edge 7 resting on the aforementioned approach and the blade lightly detached from the posterior face of the tibia, thus presenting a working area facilitating the final insertion of the PCL.

Figure 4:
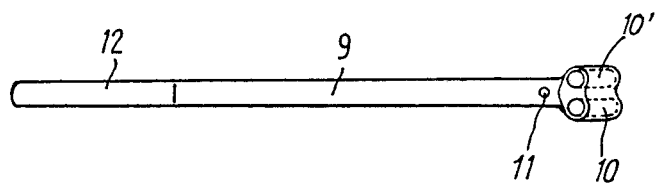
FIGS. 4 and 5 are respectively a view of the sector of the instrument comprising the double branch guide and a side view of the same instrument.
Figure 5:
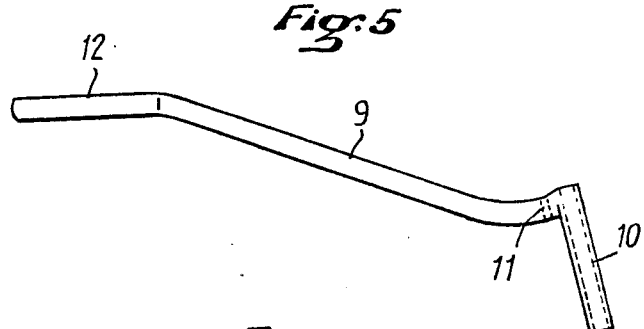

According to FIGS. 4 and 5, the guide support 9 comprises an arm in a shape designed to follow the anatomical profile of the anterior face of the tibia and supporting, at the end, two joined double branch guides 10 and 10', mounted in such a manner that, when the visor device 9 is fixed to the chisel 1, the axes of the guides 10 and 10' each culminate in a groove 6 and 6' of the sector 4 of the blade of the aforesaid chisel 1, following an oblique vertical angle of about 30 degrees (angle b).

In this arrangement, the angle (a) formed by elongation of the axis of each one of the guides and the tangent at the concave face 4 of the blade at their point of intersection is in the range of 130 degrees. The guides 10 and 10' are joined at an axis distance of 8 mm and have a useful passage between them with a diameter 5, 5 mm. Furthermore, the length of the aforementioned guides is about 50 mm thus ensuring perfect guidance for the drills 23 making the trans-tibial tunnels designed to receive the parts of the PCL.

The positioning device 9 is fitted with a terminal shank, cross section 12, fitting, at the desired moment, into the groove 12' of the same section, extending between the handle 2 and the blade of the chisel 1. A small hole 11 is advantageously situated in the arm of the guide support 9, just above the branch guides 10 and 10', making it possible to insert a steel pin 28 emplanted in the bone thus to ensure the firm holding of the entire surgical instrument positioned in accordance with FIG. 7.

One proceeds to the perforation of the two tunnels 19 and 20 crossing from each part the tibia 16. When the drill 23 culminates in the posterior face of the tibia, it aims on the concave part 4 of the chisel blade 1 thus avoiding serious wounds to the posterior vascular mass. The two trans-tibial tunnels 19 and 20 being made, the drills 23 are pulled out leaving firmly in place all of the surgical instrument according to the invention. Then one can proceed to the prosthetic replacement of the PCL of the knee by a medial anterior approach.

The parts 24 of the ligament, previously bent into a 'U' shape, are passed across the two tunnels 17 and 17' which have been previously perforated in the internal femoral condyle 13 and culminate on the extra-synovial condylar cheek 15. The two tunnels 17 and 17' present, furthermore, the particularity of possessing a common entrance 18 made in the femoral notch 14 at the anatomical point of femoral insertion of the PCL and the distinct exit orifices 17 and 17', each distanced apart by at least 10 mm.

In accordance with FIGS. 8 and 9, the bent back part 25 PCL forming the base of the 'U' is between the orifices 17 and 17', thus ensuring the immediate fixation of the PCL on the femoral section 15. The two strands 26 of the PCL culminating in the notch 4, are thus reserved. Through the trans-tibial channels 19 and 20, are threaded, through the anterior face of the tibia 16, two flexible pins terminating in an eyelet which coincides with the concave part 4 of the chisel blade 1 with only the one possibility of remounting the blade along the grooves 6 and 6', given an angle of attack of approximately 130 degrees. The aforementioned flexible pins appear above the notch 5 on the blade, in the interarticular cavity, making it possible to secure the two strands 26 ready for the eyelets of the two pins and, by reverse withdrawal of the devices and thus formed, will make the extremities of the PCL appear on the anterior-internal aspect of the tibia. The tibia 16 is thus held in position of anterior angle of 90 degrees. Some small cortico-sponge graft plugs are driven in at the anterior aspect of the tibia to the right of the tunnels 19 and 20 and packed into the aforesaid tunnels to ensure immediate fixation of the PCL. The two extremities 24 of the PCL are sufficiently extended in angle position posterior to 0 degrees, then anchored by two 6 mm surgical staples 27.

The residues of the extremities 24 extending beyond the staples are buried in the area set apart for the bone grafts which is afterwards covered over by the cruciate tendons which are reinserted in their original position.

PCL plasty of the knee carried out with the instrument which is the subject of this invention also brings about the advantage of reduced post-operative care. in particular, no immobilisation in plaster is necessary. The instrument permits the simultaneous positioning of two ligamentary parts thus endowing their insertion with an immediate solidity.

I claim:

1. Surgical instrument for positioning and insertion for plasty (or prosthetic replacement) of the posterior cruciate ligament of the knee enabling this surgery to be carried out by a medial anterior approach, whilst obtaining an anatomical point of penetration of the aforementioned PCL at the parapatellar aspect of the tibia and avoiding any damage to the posterior elements, notably vascular, the surgical instrument comprising:
    a chisel composed of a handle and a blade in the shape of an italic 'S' and having an internal terminal part that is concave, so that the aforesaid blade can be introduced across the femoral notch up to the posterior face of the tibia; and
    a guide support rigidly anchored on the chisel and which includes at its extremity a double branch guide, adapted for guiding the placement of drills into the tibial section, the angle between the axis of the guide and the tangent at the internal face of the concave part of the blade being greater than 90 degrees, thus permitting the simultaneous insertion of the two postero-internal and postero-external parts of the posterior cruciate ligament.

2. The surgical instrument of claim 1, wherein the chisel is fitted, in its terminal part, with a cutting edge in the shape of a bevelled edge enabling dissection, by scraping from top to bottom, of the elements attached to the posterior face of the tibia.

3. A surgical instrument, comprising:
    a chisel having a handle and a curved blade attached thereto, the blade being curved away from the axis of the handle in the region adjacent the handle and being concavely curved back toward the axis of the handle at its terminal end;
    a drill guide support rigidly but removably attached to the handle, the drill guide support extending from the handle a distance such that its terminal end is about as far from the handle as is the terminal end of the blade; and
    a drill guide supported on the drill guide support, the drill guide support having a pair of parallel bores therethrough disposed such that the axis of the bores intersects the blade near its terminal end.

4. The surgical instrument of claim 3, wherein the terminal end of the blade has a sharpened bevelled edge, whereby the blade can dissect elements attached to bone by scraping along the face of the bone.

5. The surgical instrument of claim 3, wherein a pair of grooves are formed in the blade adjacent the terminal end of the blade.

6. The surgical instrument of claim 3, further including a hole through the drill guide support at a location adjacent the drill guide, whereby the surgical instrument may be anchored to a bone during a surgical procedure.

7. A surgical instrument useful in repair or replacement of the posterior cruciate ligament, comprising:
    a chisel having a handle and a curved blade attached thereto, the blade being curved away from the axis of the handle in the region adjacent the handle and being curved back toward the axis of the handle at its terminal end, the blade having a bevelled terminal end so as to act as a scraper of tissue;
    a drill guide support rigidly attached to the handle, the drill guide support extending from the handle a distance such that its terminal end is about as far from the handle as is the terminal end of the blade;
    means for rigidly but removably attaching the drill guide support to the handle; and
    a drill guide supported on the drill guide support, the drill guide support having a pair of parallel bores therethrough disposed such that the axis of the bores intersects the blade near its terminal end.

* * * * *